(12) United States Patent
Benner et al.

(10) Patent No.: US 7,576,174 B2
(45) Date of Patent: *Aug. 18, 2009

(54) COMPOSITIONS CAPABLE OF REDUCING ELEVATED BLOOD UREA CONCENTRATION

(75) Inventors: Robbert Benner, Barendrecht (NL); Nisar Ahmed Khan, Rotterdam (NL)

(73) Assignee: Biotempt B.V., Koekange (NL)

( * ) Notice: Subject to any disclaimer, the term of this patent is extended or adjusted under 35 U.S.C. 154(b) by 286 days.

This patent is subject to a terminal disclaimer.

(21) Appl. No.: 11/346,450

(22) Filed: Feb. 2, 2006

(65) Prior Publication Data

US 2007/0219138 A1 Sep. 20, 2007

Related U.S. Application Data

(63) Continuation-in-part of application No. 11/249,541, filed on Oct. 13, 2005, now abandoned, which is a continuation-in-part of application No. PCT/EP2005/003707, filed on Apr. 8, 2005, and a continuation-in-part of application No. 10/821,256, filed on Apr. 8, 2004, now abandoned, and a continuation-in-part of application No. 10/262,522, filed on Sep. 30, 2002, now Pat. No. 7,365,155, which is a continuation of application No. PCT/NL01/00259, filed on Mar. 3, 2001.

(30) Foreign Application Priority Data

Mar. 29, 2000 (EP) .................................. 00201139

(51) Int. Cl.
C07K 2/00 (2006.01)
(52) U.S. Cl. .............................. 530/300; 514/2; 530/330
(58) Field of Classification Search .................. None
See application file for complete search history.

(56) References Cited

U.S. PATENT DOCUMENTS

| | | | |
|---|---|---|---|
| 4,977,244 | A | 12/1990 | Muchmore et al. |
| 5,380,668 | A | 1/1995 | Herron |
| 5,677,275 | A | 10/1997 | Lunardi-Iskandar et al. |
| 5,851,997 | A | 12/1998 | Harris |
| 5,854,004 | A | 12/1998 | Czernilofsky et al. |
| 5,877,148 | A | 3/1999 | Lunardi-Iskandar et al. |
| 5,958,413 | A | 9/1999 | Anagnostopulos et al. |
| 5,968,513 | A | 10/1999 | Gallo et al. |
| 5,997,871 | A | 12/1999 | Gallo et al. |
| 6,319,504 | B1 | 11/2001 | Gallo et al. |
| 6,361,992 | B1 | 3/2002 | Szkudlinski et al. |
| 6,489,296 | B1 | 12/2002 | Grinnell et al. |
| 6,583,109 | B1 | 6/2003 | Gallo et al. |
| 6,596,688 | B1 | 7/2003 | Gallo et al. |
| 6,620,416 | B1 | 9/2003 | Gallo et al. |
| 6,727,227 | B1 | 4/2004 | Khavinson |
| 2002/0041871 | A1 | 4/2002 | Brudnak |
| 2002/0064501 | A1 | 5/2002 | Khan et al. |
| 2003/0049273 | A1 | 3/2003 | Gallo et al. |
| 2003/0113733 | A1 | 6/2003 | Khan et al. |
| 2003/0119720 | A1 | 6/2003 | Khan et al. |
| 2003/0166556 | A1 | 9/2003 | Khan et al. |
| 2003/0186244 | A1 | 10/2003 | Margus et al. |
| 2003/0215434 | A1 | 11/2003 | Khan et al. |
| 2003/0219425 | A1 | 11/2003 | Khan et al. |
| 2003/0220257 | A1 | 11/2003 | Benner et al. |
| 2003/0220258 | A1 | 11/2003 | Benner et al. |
| 2003/0220259 | A1 | 11/2003 | Benner et al. |
| 2003/0220260 | A1 | 11/2003 | Khan et al. |
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |

FOREIGN PATENT DOCUMENTS

| | | |
|---|---|---|
| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| WO | 96/04008 | 2/1996 |
| WO | 97/49373 | 12/1997 |
| WO | 97/49418 | 12/1997 |
| WO | 97/49432 | 12/1997 |
| WO | WO 97/49721 | 12/1997 |
| WO | WO 98/35691 | 8/1998 |
| WO | WO 99/59617 | 11/1999 |
| WO | WO 01/10907 A2 | 2/2001 |
| WO | WO 01/11048 A2 | 2/2001 |
| WO | WO 01/29067 | 4/2001 |
| WO | WO 01/68113 A1 | 9/2001 |
| WO | WO 01/72831 | 10/2001 |
| WO | WO 02/085117 | 10/2002 |
| WO | WO 03/029292 A2 | 4/2003 |

OTHER PUBLICATIONS

Albini, A., et al., "Old drugs as novel angiogenesis inhibitors: Preclinical studies with NAC, hCG, EGCG and somatostatin," 17 Clinical & Experimental Metastasis 739 (1999).
Blackwell, Timothy S., et al., "The Role of Nuclear Factor-kB in Cytokine Gene Regulation," 17 Am. J. Respir. Cell Mol. Biol. 3-9 (1997).
Christman et al., Nuclear factor kappaB: a pivotal role in the systemic inflammatory response syndrome and new target for therapy, Intens Care Med, 1998, pp. 1131-1138, vol. 24.

(Continued)

Primary Examiner—Michael Szperka
Assistant Examiner—Yunsoo Kim
(74) Attorney, Agent, or Firm—TraskBritt

(57) ABSTRACT

The invention includes a method of reducing urea concentration in a subject's serum. Such a method comprises administering to the subject (e.g., a mammal such as a human) a composition comprising an oligopeptide (or oligopeptides) having activity in reducing urea concentration in the subject's serum as determined by a mouse renal reperfusion test, wherein the oligopeptide comprises the sequence AQG or MTRV (SEQ ID NO:1), AQGV (SEQ ID NO:2) or LAGV (SEQ ID NO:4).

4 Claims, 3 Drawing Sheets

OTHER PUBLICATIONS

Connelly et al., Biphasic Regulation of NF-kB Activity Underlies the Pro- and Anti-Inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Iskandar et al., "Effects of a urinary factor from women in early pregnancy on HIV-1. SIV and associated disease", Nature Medicine, Apr. 1998, vol. 4, No. 4, pp. 428-434.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Keller, S., et al., "Human Chorionic Gonadotropin (hCG) Is a Potent Angiogenic Factor for Uterine Endothelial Cells in Vitro," 20(5-6) Placenta, p. A37 (Jul. 1999).

Khan, Nisar A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Lang et al., "Induction of apoptosis in Kaposi's sarcoma spindle cell cultures by the subunits of human chorionic gonadotropin", AIDS 1997, vol. 11, No. 11, pp. 1333-1340.

Medzhitov, Toll-like Receptors and Innate Immunity, Nature Reviews/Immunology, Nov. 2001, pp. 135-145, vol. 1.

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Patil, A., et al., "The Study of the Effect of Human Chorionic Gonadotrophic (HCG) Hormone on the Survival of Adrenal Medulla Transplant in Brain. Preliminary Study," 87 Acta Neurochir (WIEN) 76-78 (1987).

Rohrig et al., Growth-stimulating Influence of Human Chorionic Gonadotropin (hCG) on Plasmodium falciparum in vitro, Zentralblatt Bakt, 1999, pp. 89-99, vol. 289.

Slater, Lewis M., et al., "Decreased Mortality of Murine Graft-VersUS -Host Disease by Human Chorionic gonadotropin,"23(1) Transplantation 103-104 (Jan. 1977).

Tak et al., NF-kappaβ: a key role in inflammtory diseases, J Clin Invest., 2001, pp. 7-11, vol. 107.

Tan et al., The role of activation of nuclear factor-kappa B of rat brain in the pathogenesis of experimental allergic encephalomyelitis, Acta Physiol Sinica, 2003, pp. 58-64, vol. 55.

Tovey et al., Mucosal Cytokine Therapy: Marked Antiviral and Antitumor Activity, J. Interferon Cytokine Res., 1999, pp. 911-921, vol. 19.

Wulczyn, F. Gregory, et al., "The NF-kB/Rel and IkB gene families: mediators of immune response and inflammation," 74(12) J. Mol. Med. 749-769 (1996).

Yamamoto, Y., et al., "Role of the NF-kB Pathway in the Pathogenesis of Human Disease States," 1(3) Current Molecular Medicine 287-296 (Jul. 2001).

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Divison Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunopharmac., 1997, pp. 501-505, vol. 19, No. 9/10.

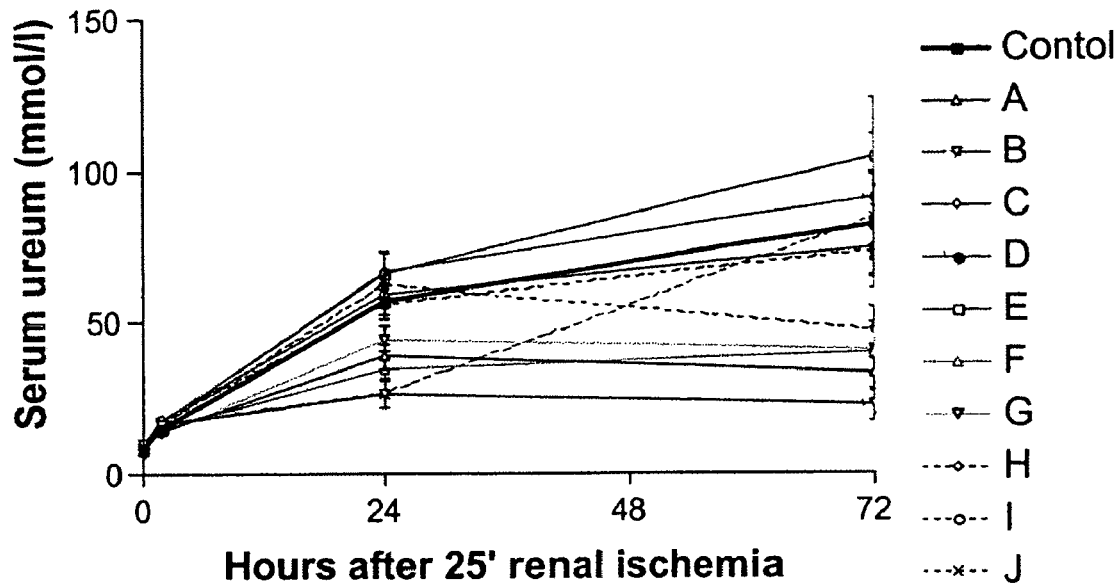

Op 24 uur post-reperfusie:
(C-term: CARBOXYL; N-term: FREE)
- A   p=0.0491 NMPF-47 LAGV
- B   p=0.0008 NMPF-46 AQGV
- C   p=0.9248 NMPF-44 LAG
- D   p=0.4043 NMPF-43 AQG
- E   p=0.1848 NMPF-12 MTR
- F   p=0.0106 NMPF-11 MTRV
- G   p=0.1389 NMPF-7 VLPALPQ
- H   p=0.5613 NMPF-6 VLPALP
- I   p=0.9301 NMPF-4 LQGV
- J   p=0.0030 NMPF-3 LQG Op 72 uur post-reperfusie:
(C-term: CARBOXYL; N-term: FREE)
- A   p=0.0017 NMPF-47 LAGV
- B   p<0.0001 NMPF-46 AQGV
- C   p=0.8186 NMPF-44 LAG
- D   p=0.2297 NMPF-43 AQG
- E   p=0.0242 NMPF-12 MTR
- F   p=0.0021 NMPF-11 MTRV
- G   p=0.0049 NMPF-7 VLPALPQ
- H   p=0.3297 NMPF-6 VLPALP
- I   p=0.8328 NMPF-4 LQGV
- J   p=0.9445 NMPF-3 LQG

COMPOSITIONS CAPABLE OF REDUCING ELEVATED BLOOD UREA CONCENTRATION

CROSS-REFERENCE TO RELATED APPLICATIONS

This application is a continuation-in-part of U.S. patent application Ser. No. 11/249,541, filed on Oct. 13, 2005 now abandoned, which is a continuation-in-part of International Application No. PCT/EP2005/003707, filed on Apr. 8, 2005, designating the United States of America, U.S. patent application Ser. No. 10/821,256, filed on Apr. 8, 2004 now abandoned, and U.S. patent application Ser. No. 10/262,522, filed on Sep. 30, 2002 now U.S. Pat. No. 7,365,155, which itself is a continuation of International Application No. PCT/NL01/00259, (International Publication No. WO 01/72831 A2) filed Mar. 3, 2001, designating the United States of America, the contents of the entirety of all of which are incorporated by this reference.

TECHNICAL FIELD

The invention relates generally to biotechnology, and more specifically to compositions having immunoregulatory activity, which compounds include particular oligopeptides derived from human chorionic gonadotropin ("hCG").

BACKGROUND

U.S. Pat. No. 5,380,668 to Herron (Jan. 10, 1995), the contents of the entirety of which are incorporated by this reference, discloses, among other things, various compounds having the antigenic binding activity of hCG. The oligopeptides disclosed therein are disclosed generally for use in diagnostic methods.

Various patents and patent applications to Gallo et al. (e.g., U.S. Pat. No. 5,677,275 (corresponding to WO 96/04008 A1), U.S. Pat. No. 5,877,148 (also corresponding to WO 96/04008 A1), WO 97/49721 A1, U.S. Pat. No. 6,319,504 (corresponding to WO 97/49373), U.S. Patent Application 2003/0049273 A1 (also corresponding to WO 97/49373), U.S. Pat. No. 5,968,513 (corresponding to WO 97/49418), U.S. Pat. No. 5,997,871 (corresponding to WO 97/49432), U.S. Pat. Nos. 6,620,416, 6,596,688, WO 01/11048 A2, WO 01/10907 A2., and U.S. Pat. No. 6,583,109) relate to various oligopeptides and their use in, among other things, "inhibiting HIV infection," "treating or preventing HIV infection," "treating or preventing cancer," "treating or preventing a condition characterized by loss of body cell mass," "treating or preventing a condition associated with pathological angiogenesis," "treating or preventing hematopoietic deficiency," "ex vivo gene therapy," "expanding blood cells in vitro," and/or "providing blood cells to a subject."

DISCLOSURE OF THE INVENTION

As described in PCT International Publication No. WO 03/029292 A2 (published Apr. 10, 2003), PCT International Publication No. WO 01/72831 A2 (published Oct. 4, 2001), and U.S. Patent Application Publications 20020064501 A1 (published May 30, 2002), 20030119720 A1 (published Jun. 26, 2003), 20030113733 A1 (published Jun. 19, 2003), and 20030166556 A1 (published Sep. 4, 2003), the contents of all of which are incorporated by this reference, compositions containing some of the oligopeptides described herein have immunoregulatory activity useful in, for example, the treatment of sepsis and other disease states and conditions.

The invention includes a method of reducing blood urea nitrogen (BUN) concentration (herein also called urea concentration) in a subject's serum. Such a method comprises administering to the subject (e.g., a mammal such as a human) a composition comprising an oligopeptide (or oligopeptides) having activity in reducing urea concentration in the subject's serum as determined by a mouse renal reperfusion test, wherein the oligopeptide comprises the sequence AQG or LAGV (SEQ ID NO:4), or AQGV (SEQ ID NO:2) or MTRV (SEQ ID NO:1)).

The oligopeptide of the composition will typically be from three (3) to twelve (12) amino acids in length. In the case where the composition includes the oligopeptide AQG or LAGV (SEQ ID NO:4) or AQGV (SEQ ID NO:2), the composition may be administered orally. The oligopeptide will preferably be of synthetic origin (e.g., produced by a Merrifield synthesis). When the composition is administered to the subject parenterally, the composition will typically consist essentially of oligopeptide and PBS (e.g., in an amount of from about 0.25 to about 10 mg/kg body mass of the subject).

The invention is thought to be useful for instances, when, for example, the subject is undergoing acute renal failure, especially when the subject is undergoing persistent oliguria, is not producing more than ½ ml urine per hour per kilogram body mass of the subject, and/or has a serum potassium level greater than 6.5 mmol per liter serum.

In one preferred embodiment, the invention involves administering a purified, synthetic or isolated peptide consisting of AQGV (SEQ ID NO:2), or an acid addition salt thereof. A typical dosage of this peptide will vary from about 0.5 to about 35 mg/kg body weight of the subject In another preferred embodiment, typically when a relatively low dosage is preferred, the invention involves administering a purified, synthetic or isolated peptide consisting of AQG, or an acid addition salt thereof at, for example, a dosage of the peptide from about 0.1 to about 10 mg/kg body weight of the subject.

The invention also provides use of a composition according to the invention for the preparation of a pharmnaceutical composition or medicament for the treatment of a disorder such as acute renal failure. Such a composition is preferably prepared using a purified, synthetic or isolated peptide consisting of AQG or AQGV (SEQ ID NO:2) or LAGV (SEQ ID NO:4) or MTRV (SEQ ID NO:1), or an acid addition salt thereof. Most preferably, AQG (when low dosages are preferred) or AQGV (SEQ ID NO:2) is used.

BRIEF DESCRIPTION OF THE FIGURES

FIG. 1 graphically depicts the results of Example 1. Shown are the BUN (urea) values at the various points in time after treatment with peptides A to F or without treatment (control).

DETAILED DESCRIPTION OF THE INVENTION

Figure 2:
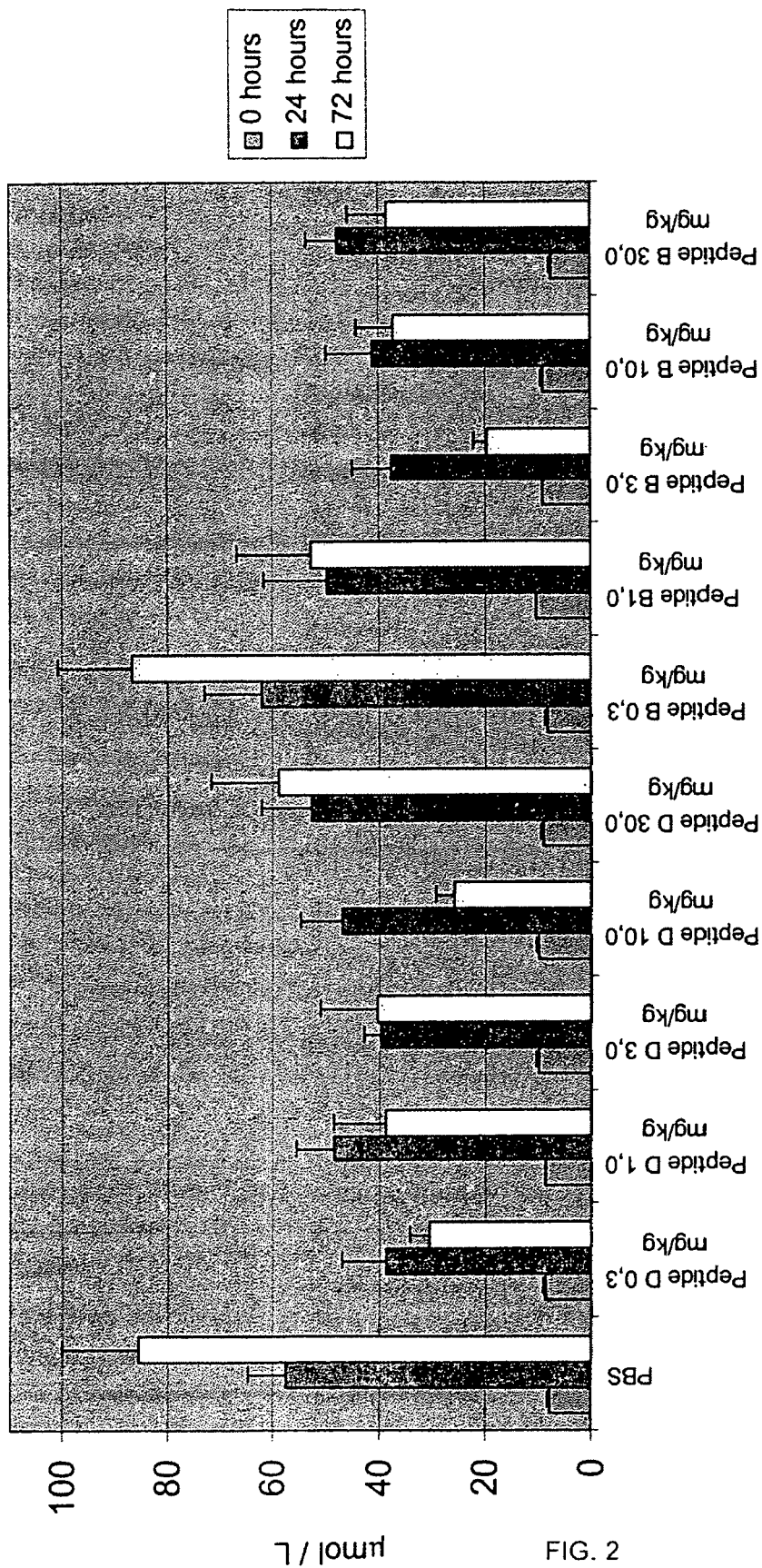
FIG. 2 graphically depicts the results of Example 4. Shown are the BUN (urea) values at the various points in time after treatment with varying dosages of peptide D or peptide B or without treatment (PBS).

As used herein, a "purified, synthetic or isolated" peptide is one that has been purified from a natural or biotechnological source, or, more preferably, is synthesized as described herein.

"Composition," as used herein, refers to chemical compounds that contain or consist of the oligopeptide. The oligopeptide is preferably isolated before inclusion within the composition. The oligopeptide most preferably consists of three (3) to six (6) amino acids.

For instance, the previously described preferred compound could, in one embodiment be:

NT A Q G V CT wherein NT at the N-terminus is selected from the group of H—, CH3—, an acyl group, or a general protective group; and CT at the C-terminus is selected from the group of small (e.g. 1 to 5 amino acids) peptides, —OH, —OR$^1$, —NH$_2$, —NHR$^1$, —NR$^1$R$^2$, or —N(CH$_2$)$_{1-6}$NR$^1$R$^2$, wherein R$^1$R$^2$, when present, are independently selected from H, alkyl, aryl, (ar)alkyl, and wherein R$^1$R$^2$, can be cyclically bonded to one another.

"Alkyl" as used herein, is preferably a saturated branched or unbranched hydrocarbon having one to six carbon atoms, for example, methyl, ethyl, and isopentyl.

"Aryl" as used herein, is an aromatic hydrocarbon group, preferably having 6 to 10 carbon atoms, such as phenyl or naphthyl.

"(Ar)alkyl" as used herein, is an arene group (having both aliphatic and aromatic portions), preferably having 7 to 13 carbon atoms such as benzyl, ethylbenzyl, n-propylbenzyl, and isobutylbenzyl.

"Oligopeptide" as used herein, are peptides having from 3 to 12 amino acids joined together by peptide bonds. Equivalent to oligopeptides are compounds having the same or equivalent side chains as the particular amino acids used in an oligopeptide, and arranged sequentially in the same order as the peptides, but joined together by non-peptide bonds, e.g., by isosteric linkages such as the keto isostere, hydroxy isostere, diketo isostere, or the keto-difluoromethylene isostere.

"Composition" also includes, for example, an acceptable salt of the oligopeptide or a labeled oligopeptide. As used herein, "acceptable salt" refers to salts that retain the desired activity of the oligopeptide or equivalent compound, but preferably do not detrimentally affect the activity of the oligopeptide or other component of a system in which uses the oligopeptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt).

The invention also provides use of an oligopeptide having activity in reducing urea concentration in a subject's serum as determined by a mouse renal reperfusion test, the oligopeptide preferably comprising the sequence AQG or MTRV (SEQ ID NO:1) or LAGV (SEQ ID NO:4), in the production of a pharmaceutical composition for reducing urea concentration in a subject's serum, in particular when the subject is undergoing acute renal failure. It is preferred that the oligopeptide to be used in the production of the pharmaceutical composition consists of AQGV (SEQ ID NO:2).

Such a pharmaceutical composition may be administered to the subject parenterally or orally. Such a pharmaceutical composition may consist essentially of oligopeptide and PBS. It is preferred that the oligopeptide is of synthetic origin.

Suitable treatment for example entails administering the oligopeptide in the pharmaceutical composition to the patient intravenously in an amount of from about 0.1 to about 35 mg/kg body mass of the subject. It may be useful that the pharmaceutical composition consists essentially of from one to three different oligopeptides.

Such treatment is in particular preferred when the subject is undergoing persistent oliguria, for example when the subject's kidneys are not producing more than ½ ml urine per hour per kilogram body mass of the subject, or when the subject has a serum potassium level greater than 6.5 mmol per liter serum.

The thus developed chemical entity can be administered and introduced in-vivo systemically, topically, or locally. The peptide, or its modification or derivative, can be administered as the entity as such or as a pharmaceutically acceptable acid- or base addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

A "substitution" with regard to the various amino acids generally relate to substituting a group such as alkoxy, halogen, hydroxy, nitro, or lower alkyl onto an aromatic ring for hydrogen that would usually be present. Substitutions can also be made on the alkyl chain connecting the aromatic portion to the peptide backbone, with, for instance lower alkyl groups substituting for hydrogen. Still further substitutions can be made at the alpha position of an amino acid, also using an alkyl group.

Preferred substitutions involve the use of fluorine or chlorine as a halogen, and methoxy as an alkoxy group. With regard to alkyl and lower alkyl, generally alkyl groups having fewer (1 to 3) carbon atoms are preferred.

The compounds according to the general formula may be prepared in a manner conventional for such compounds. To that end, suitably N alpha protected (and side-chain protected if reactive side-chains are present) amino acid derivatives or peptides are activated and coupled to suitably carboxyl protected amino acid or peptide derivatives either in solution or on a solid support. Protection of the alpha-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The Z group can also be removed by catalytic hydrogenation. Other suitable protecting groups include the Nps, Bmv, Bpoc, Aloc, MSC, etc. A good overview of amino protecting groups is given in *The peptides, Analysis, Synthesis, Biology*, Vol. 3 E. Gross and J. Meienhofer, eds. (Academic Press, New York, 1981). Protection of carboxyl groups can take place by ester formation, for example, base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology*, id. or in *Pure and Applied Chemistry*, 59(3), 331-344 (1987). Activation of the carboxyl group of the suitably protected amino acids or peptides can take place by the azide, mixed anhydride, active ester, or carbodiimide method especially with the addition of catalytic and racemization-suppressing compounds like 1-N-N-hydroxybenzotriazole, N-hydroxysuccinimide, 3-hydroxy-4-oxo-3,4-dihydro-1,2,3,-benzotriazine, N-hydroxy-5norbomene-2,3-dicarboxyimide. Also the anhydrides of phosphorus based acids can be used. See, e.g., *The Peptides, Analysis, Synthesis, Biology*, supra and *Pure and Applied Chemistry*, 59(3), 331-344 (1987).

It is also possible to prepare the compounds by the solid phase method of Merrifield. Different solid supports and different strategies are known see, e.g. Barany and Merrifield in *The Peptides, Analysis, Synthesis, Biology*, Vol. 2, E. Gross and J. Meienhofer, eds. (Acad. Press, New York, 1980), Kneib-Cordonier and Mullen *Int. J. Peptide Protein Res.*, 30, 705-739 (1987) and Fields and Noble *Int. J. Peptide Protein Res.*, 35, 161-214 (1990). The synthesis of compounds in which a peptide bond is replaced by an isostere, can, in general, be performed using the previously described protecting groups and activation procedures. Procedures to synthesize the modified isosteres are described in the literature e.g. for the —$CH_2$—NH— isostere and for the —CO—$CH_2$— isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g. volumes 3, 5 and 9 of the series on *The Peptides Analysis, Synthesis, Biology*, supra.

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds. (Acad. Press, New York, 1987).

Although possibly not desirable from an economic point of view, oligopeptides according to the invention could also be made according to recombinant DNA methods. Such methods involve the preparation of the desired oligopeptide thereof by means of expressing recombinant polynucleotide sequence that codes for one or more of the oligopeptides in question in a suitable microorganism as host. Generally the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eucaryotic or prokaryotic host cell, and culturing the host cell thus transformed. When a eucaryotic host cell is used, the compound may include a glycoprotein portion.

As used herein, a "functional analogue" or "derivative" of a peptide includes an amino acid sequence, or other sequence monomers, which has been altered such that the functional properties of the sequence are essentially the same in kind, not necessarily in amount. An analogue or derivative can be provided in many ways, for instance, through "conservative amino acid substitution." Also peptidomimetic compounds can be designed that functionally or structurally resemble the original peptide taken as the starting point but that are for example composed of non-naturally occurring amino acids or polyamides. With "conservative amino acid substitution," one amino acid residue is substituted with another residue with generally similar properties (size, hydrophobicity), such that the overall functioning is likely not to be seriously affected. However, it is often much more desirable to improve a specific function. A derivative can also be provided by systematically improving at least one desired property of an amino acid sequence. This can, for instance, be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

A derivative or analogue can also be, for instance, generated by substitution of an L-amino acid residue with a D-amino acid residue. This substitution, leading to a peptide that does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics.

A person skilled in the art is well able to generate analogous compounds of an amino acid sequence. This can, for instance, be done through screening of a peptide library. Such an analogue has essentially the same functional properties of the sequence in kind, not necessarily in amount. Also, peptides or analogues can be circularized, for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation.

Synthetic versions of these oligopeptides as described above, and functional analogues or derivatives or breakdown products, are herein provided to lower BUN concentration be used in methods to the treatment of disease.

The term "pharmaceutical composition" as used herein is intended to cover both the active composition of the invention alone or a composition containing the composition of the invention together with a pharmaceutically acceptable carrier, diluent or excipient. Acceptable diluents of an oligopeptide as described herein in the detailed description are for example physiological salt solutions or phosphate buffered salt solutions. In one embodiment, an oligopeptide or composition is administered in an effective concentration to an animal or human systemically, for example, by intravenous, intra-muscular or intraperitoneal administration. Another way of administration comprises perfusion of organs or tissue, be it in vivo or ex vivo, with a perfusion fluid comprising an oligopeptide or composition according to the invention. The administration may be done as a single dose, as a discontinuous sequence of various doses, or continuously for a period of time sufficient to permit substantial modulation of gene expression. In the case of a continuous administration, the duration of the administration may vary depending upon a number of factors that would readily be appreciated by those skilled in the art.

The administration dose of the active molecule may be varied over a fairly broad range. The concentrations of an active molecule that can be administered would be limited by efficacy at the lower end and the solubility of the compound at the upper end. The optimal dose or doses for a particular patient should and can be determined by the physician or medical specialist involved, taking into consideration well-known relevant factors such as the condition, weight and age of the patient, etc.

The active molecule may be administered directly in a suitable vehicle, such as, for example, phosphate-buffered saline ("PBS") or solutions in alcohol or DMSO. Pursuant to preferred embodiments of the present invention, however, the active molecule is administered through a single dose delivery using a drug-delivery system. A suitable drug-delivery system would be pharmacologically inactive or at least tolerable. It should preferably not be immunogenic nor cause inflammatory reactions, and should permit release of the active molecule so as to maintain effective levels thereof over the desired time period. Alternatives are known in the art as suitable for purposes of sustained release and are contemplated as within the scope of the present invention. Suitable delivery vehicles include, but are not limited to, the following: microcapsules or microspheres; liposomes and other lipid-based release systems; viscous instillates; absorbable and/or biodegradable mechanical barriers and implants; and polymeric delivery materials, such as polyethylene oxide/ polypropylene oxide block copolymers, polyesters, cross-linked polyvinyl alcohols, polyanhydrides, polymethacrylate and polymethacrylamide hydrogels, anionic carbohydrate polymers, etc. Useful delivery systems are well known in the art.

One formulation to achieve the active molecule release comprises injectable microcapsules or microspheres made from a biodegradable polymer, such as poly(dl-lactide), poly (dl-lactide-co-glycolide), polycaprolactone, polyglycolide, polylactic acid-co-glycolide, poly(hydroxybutyric acid), polyesters or polyacetals. Injectable systems comprising microcapsules or microspheres having a diameter of about 50 to about 500 micrometers offer advantages over other delivery systems. For example, they generally use less active molecules and may be administered by paramedical personnel. Moreover, such systems are inherently flexible in the design of the duration and rate of separate drug release by selection of microcapsule or microsphere size, drug loading and dosage administered. Further, they can be successfully sterilized by gamma irradiation.

The design, preparation, and use of microcapsules and microspheres are well within the reach of persons skilled in the art and detailed information concerning these points is available in the literature. Biodegradable polymers (such as lactide, glycolide and caprolactone polymers) may also be used in formulations other than microcapsules and microspheres; e.g., pre-made films and spray-on films of these polymers containing the active molecule would be suitable for use in accordance with the present invention. Fibers or filaments comprising the active molecule are also contemplated as within the scope of the present invention.

Another highly suitable formulation for a single-dose delivery of the active molecule in accordance with the present invention involves liposomes. The encapsulation of an active molecule in liposomes or multilamellar vesicles is a well-known technique for targeted drug delivery and prolonged drug residence. The preparation and use of drug-loaded liposomes is well within the reach of persons skilled in the art and well documented in the literature.

Yet another suitable approach for single-dose delivery of an active molecule in accordance with the present invention involves the use of viscous installates. In this technique, high molecular weight carriers are used in admixture with the active molecule, giving rise to a structure that produces a solution with high viscosity. Suitable high molecular weight carriers include, but are not limited to, the following: dextrans and cyclodextrans; hydrogels; (cross-linked) viscous materials, including (cross-linked) viscoelastics; carboxymethylcellulose; hyaluronic acid; and chondroitin sulfate. The preparation and use of drug-loaded viscous instillates is well known to persons skilled in the art.

Pursuant to yet another approach, the active molecule may be administered in combination with absorbable mechanical barriers such as oxidized regenerated cellulose. The active molecule may be covalently or non-covalently (e.g., ionically) bound to such a barrier, or it may simply be dispersed therein.

The invention is further explained with the aid of the following illustrative examples.

EXAMPLES

Example 1

Six oligopeptides (i.e., A: LAGV (SEQ ID NO:4), B: AQGV (SEQ ID NO:2), C: LAG, D: AQG, E: MTR, and F: MTRV (SEQ Ip NO:1)) were tested and compared with PBS (control) in a double blind animal study for each peptide's relative ability to aid recovery in a mouse renal ischemia reperfusion test. In this test, the mice were anesthetized, and one kidney from each mouse was removed. The other kidney was tied off for 25 minutes, and the serum urea levels were allowed to increase. Both before and after tying off, each of the separate peptides was administered to thirty (30) different mice (5 mg oligopeptide/kg body mass intravenously), after which, the mortality of the mice was determined for each oligopeptide as well as was the BUN concentration at two hours, 24 hours and 72 hours. The results are shown in FIG. 1 and (excluding the results of peptide A (LAGV (SEQ ID NO:4)) obtained in example 1) in Table 2 below.

Under inhalation anesthesia, the left kidney with its artery and vein was isolated and occluded for 25 minutes using a microvascular clamp. During surgery animals were placed on a heating path to maintain body temperature at 37° C. Five minutes before placing the clamp, and 5 minutes before releasing the clamp, 5 mg/kg of peptide, dissolved in 0.1 mL of sterile saline, was administered intravenously. After reperfusion of the left kidney the right kidney was removed. Kidney function was assessed by measuring blood urea nitrogen before clamping, and at 2, 24, and 72 hours after reperfusion.

TABLE 1

Results - (mortality at 72 hours post-reperfusion).

| | PBS | A (LAGV) (SEQ ID NO: 4) | B (AQGV) (SEQ ID NO: 2) | C (LAG) | D (AQG) | E (MTR) | F (MTRV) (SEQ ID NO: 1) |
|---|---|---|---|---|---|---|---|
| | 6/10 | 6/10 | 0/10 | 4/10 | 4/10 | 4/10 | 2/10 |
| *P < (vs PBS) | | NS | 0.01 | 0.01 | 0.01 | 0.01 | 0.01 |

*2 × 2 Chi-square test. df = 1

Peptide A (SEQ ID NO:4) was the first peptide administered in the renal ischemia reperfusion test. The personnel who performed the experiments went through a learning curve while working with peptide A (SEQ ID NO:4). During administration of the peptide in the inferior caval vein, some animals experienced moderate blood loss from the site of injection, whereas others did not. Inadvertently the animals were returned to the stable without drinking water present in their cages the first night after surgery. Also, by mistake, the animals that were intended to be sacrificed at 72 h were killed 48 h after reperfusion. None of these or other problems were encountered during the experiments with peptides B-F. (See, Example 2)

As can be seen, mice administered the oligopeptides MTRV (SEQ ID NO:1) and especially AQGV (SEQ ID NO:2) did much better in terms of both survival (a significant reduction in mortality versus the PBS control group) and reduced BUN concentration than the control group (PBS) or the group administered the other oligopeptides, with more mice surviving and the serum urea levels being much lower than in the other groups. However, the oligopeptides LAG, AQG, and MTR, in this experiment having no reducing effect on BUN concentration, each caused a significant reduction of mortality compared to the PBS control, where MTR did significantly raise BUN levels in the tested mice at 72 hrs.

Example 2

One oligopeptide (A: (LAGV (SEQ ID NO:4))) was retested for its capacity to reduce BUN levels in the mice test for the reasons as described above. The results are shown in Table 2 below. As can be seen, mice administered the oligopeptide LAGV (SEQ ID NO:4) now did much better in terms of both survival (a significant reduction in mortality versus the PBS control group) and reduced BUN concentration than the control group (PBS).

Example 3

Four additional oligopeptides (G (VLPALPQ (SEQ ID NO:5)), H (VLPALP (SEQ ID NO:6)), I LQGV (SEQ ID NO:3) and J (LQG)) were tested for there capacity to reduce BUN levels in the mice test as described above. The results are shown in Table 2 below. As can be seen, mice administered the oligopeptide LQG did show reduced BUN concentration early in the experiment (at 24 hours post-reperfusion) and mice administered VLPALPQ (SEQ ID NO:5) did much better in terms of reduced BUN concentration late in the experiment (at 72 hours post-reperfusion) than the control group (PBS) or the group administered the other oligopeptides, with more mice surviving and the serum urea levels being much lower than in the other groups.

TABLE 2

BUN after 25 min renal ischemia tested in mice with peptides A-J

| Peptide | | t = 0 hr | 2 hr | 24 hr | 72 hr | C-term: N-term: | CARBOXYL FREE |
|---|---|---|---|---|---|---|---|
| A | Mean | 8.166667 | 14.03333 | 38.86364 | 32.8875 | NMPF-47 | LAGV (SEQ ID NO: 4) |
|   | sd | 1.774658 | 1.011599 | 14.54711 | 14.31228 | | |
|   | N | 18 | 3 | 11 | 8 | | |
| B | Mean | 9.713333 | 16.62 | 26.36 | 22.31 | NMPF-46 | AQGV (SEQ ID NO: 2) |
|   | sd | 1.882722 | 2.185203 | 20.62105 | 15.96444 | | |
|   | N | 30 | 10 | 20 | 10 | | |
| C | Mean | 10.15185 | 18.13333 | 59.24375 | 74.4 | NMPF-44 | LAG |
|   | SD | 1.789794 | 1.88326 | 16.19662 | 33.12546 | | |
|   | N | 29 | 6 | 16 | 6 | | |
| D | Mean | 9.303846 | 17.7 | 66.75625 | 91.18333 | NMPF-43 | AQG |
|   | SD | 1.502127 | 1.561135 | 24.50445 | 51.22154 | | |
|   | N | 26 | 8 | 16 | 6 | | |
| E | mean | 8.403846 | 17.13 | 66.23333 | 104.0167 | NMPF-12 | MTR |
|   | SD | 1.739076 | 1.625526 | 17.55069 | 48.97193 | | |
|   | N | 26 | 10 | 6 | 6 | | |
| F | mean | 7.462963 | 15.08571 | 34.57368 | 39.8375 | NMPF-11 | MTRV(SEQ ID NO: 1) |
|   | SD | 1.338526 | 1.422941 | 15.18083 | 21.45973 | | |
|   | N | 30 | 7 | 18 | 8 | | |
| G | mean | 8.256667 | 13.58 | 37.79375 | 37.6375 | NMPF-7 | VLPALPQ (SEQ ID NO: 5) |
|   | SD | 1.304021 | 1.927462 | 18.33007 | 29.32872 | | |
|   | N | 30 | 7 | 18 | 8 | | |
| H | mean | 8.423333 | 16.24 | 62.4 | 47.05 | NMPF-6 | VLPALP (SEQ ID NO: 6) |
|   | SD | 1.255521 | 1.370482 | 13.33867 | 20.92728 | | |
|   | N | 30 | 10 | 9 | 7 | | |
| I | mean | 7.518182 | 17.53333 | 56.08333 | 73.17778 | NMPF-4 | LQGV (SEQ ID NO: 3) |
|   | SD | 1.537356 | 2.956913 | 14.53573 | 23.3083 | | |
|   | N | 22 | 3 | 18 | 9 | | |
| J | mean | 7.82069 | 16.75 | 26.74 | 83.95714 | NMPF-3 | LQG |
|   | SD | 1.330515 | 1.44123 | 15.51796 | 40.32129 | | |
|   | N | 29 | 8 | 9 | 8 | | |
| PBS control | mean | 8.172414 | 15.0875 | 56.81 | 82.075 | | |
|   | SD | 1.549169 | 2.215167 | 22.4659 | 34.82713 | | |
|   | N | 29 | 8 | 15 | 4 | | |

At 24 hour post-reperfusion statistical analyses revealed P-values of:

```
A   p = 0.0491  NMPF-47  LAGV      (SEQ ID NO:4)
B   p = 0.0008  NMPF-46  AQGV      (SEQ ID NO:2)
C   p = 0.9248  NMPF-44  LAG
D   p = 0.4043  NMPF-43  AQG
E   p = 0.1848  NMPF-12  MTR
F   p = 0.0106  NMPF-11  MTRV      (SEQ ID NO:1)
G   p = 0.1389  NMPF-7   VLPALPQ   (SEQ ID NO:5)
H   p = 0.5613  NMPF-6   VLPALP    (SEQ ID NO:6)
I   p = 0.9301  NMPF-4   LQGV      (SEQ ID NO:3)
J   p = 0.0030  NMPF-3   LQG
```

At 24 hour post-reperfusion statistical analyses revealed P-values of:

```
A   p = 0.0017  NMPF-47  LAGV      (SEQ ID NO:4)
B   p < 0.0001  NMPF-46  AQGV      (SEQ ID NO:2)
C   p = 0.8186  NMPF-44  LAG
D   p = 0.2297  NMPF-43  AQG
E   p = 0.0242  NMPF-12  MTR
F   p = 0.0021  NMPF-11  MTRV      (SEQ ID NO:1)
G   p = 0.0049  NMPF-7   VLPALPQ   (SEQ ID NO:5)
H   p = 0.3297  NMPF-6   VLPALP    (SEQ ID NO:6)
I   p = 0.8328  NMPF-4   LQGV      (SEQ ID NO:3)
J   p = 0.9445  NMPF-3   LQG
```

P values were calculated by Mann Whitney U-test (SPSS for Windows).

Example 4

To determine dose-response relationships, two peptides (D (AQG, having a good effect on mortality on the mice tested in Example 1) and B (AQGV (SEQ ID NO:2), also having superior effect on BUN of the mice tested in Example 1) were also tested in a dose-response manner in the mice test as described above. Peptides were tested at 0.3, 1, 3, 10 and 30 mg/kg dosages given as described in Example 1. The results can be seen in FIG. 2. P values (calculated by Mann Whitney U-test (SPSS for Windows)) of serum urea levels of PBS compared to peptide D groups at 72 hours post-clamping were at 0.3 mg/kg 0.001, at 1 mg/kg 0.009, at 3 mg/kg 0.02, at 10 mg/kg 0.000, and at 30 mg/kg 0.23, for peptide B groups these P-values were 0.88, 0.054, 0.000, 0.001 and 0.003. As can be seen, peptide D (AQG) did reduce BUN levels surprisingly well at the lower dosages tested, as compared with peptide B (AQGV (SEQ ID NO:2)), while the beneficial effect on mortality was also still notable at the lower dosages tested.

TABLE 3

Mortality in dose-response experiment

|  | 24 h | 72 h |
| --- | --- | --- |
| PBS | 0-9 | 4-8 |
| AQG 0.3 mg/kg | 0-10 | 2-8 |
| AQG 1.0 mg/kg | 0-10 | 1-8 |
| AQG 3.0 mg/kg | 0-10 | 0-10 |
| AQG 10.0 mg/kg | 0-8 | 1-10 |
| AQG 30.0 mg/kg | 0-8 | 1-8 |
| AQGV (SEQ ID NO: 2) 0.3 mg/kg | 0-9 | 2-10 |
| AQGV (SEQ ID NO: 2) 1.0 mg/kg | 0-10 | 1-8 |
| AQGV (SEQ ID NO: 2) 3.0 mg/kg | 1-10 | 0-10 |
| AQGV (SEQ ID NO: 2) 10.0 mg/kg | 0-10 | 0-8 |
| AQGV (SEQ ID NO: 2) 30.0 mg/kg | 0-8 | 3-10 |

TABLE 4

Urea Levels in dose-response experiment

|  | 24 h | 72 h |
| --- | --- | --- |
| PBS | 57.8 | 85.4 |
| Peptide D (AQG) 0.3 mg/kg | 38.4 | 30.4 |
| Peptide D (AQG) 1.0 mg/kg | 48.4 | 38.4 |
| Peptide D (AQG) 3.0 mg/kg | 39.3 | 40.3 |
| Peptide D (AQG) 10.0 mg/kg | 46.8 | 25.8 |
| Peptide D (AQG) 30.0 mg/kg | 52.8 | 58.9 |
| Peptide B (AQGV (SEQ ID NO: 2)) 0.3 mg/kg | 62.4 | 86.7 |
| Peptide B (AQGV (SEQ ID NO: 2)) 1.0 mg/kg | 50.0 | 52.6 |
| Peptide B (AQGV (SEQ ID NO: 2)) 3.0 mg/kg | 37.4 | 19.6 |
| Peptide B (AQGV (SEQ ID NO: 2)) 10.0 mg/kg | 41.2 | 37.1 |
| Peptide B (AQGV (SEQ ID NO: 2)) 30.0 mg/kg | 47.8 | 38.0 |
| standard error | | |
| PBS | 7.1 | 14.7 |
| Peptide D (AQG) 0.3 mg/kg | 8.6 | 3.5 |
| Peptide D (AQG) 1.0 mg/kg | 7.2 | 10.2 |
| Peptide D (AQG) 3.0 mg/kg | 3.5 | 10.7 |
| Peptide D (AQG) 10.0 mg/kg | 8.0 | 3.4 |
| Peptide D (AQG) 30.0 mg/kg | 9.5 | 12.9 |
| Peptide B (AQGV (SEQ ID NO: 2)) 0.3 mg/kg | 10.8 | 14.1 |
| Peptide B (AQGV (SEQ ID NO: 2)) 1.0 mg/kg | 11.7 | 14.3 |
| Peptide B (AQGV (SEQ ID NO: 2)) 3.0 mg/kg | 7.6 | 2.6 |
| Peptide B (AQGV (SEQ ID NO: 2)) 10.0 mg/kg | 8.5 | 6.9 |
| Peptide B (AQGV (SEQ ID NO: 2)) 30.0 mg/kg | 5.8 | 7.8 |

Figure 3:
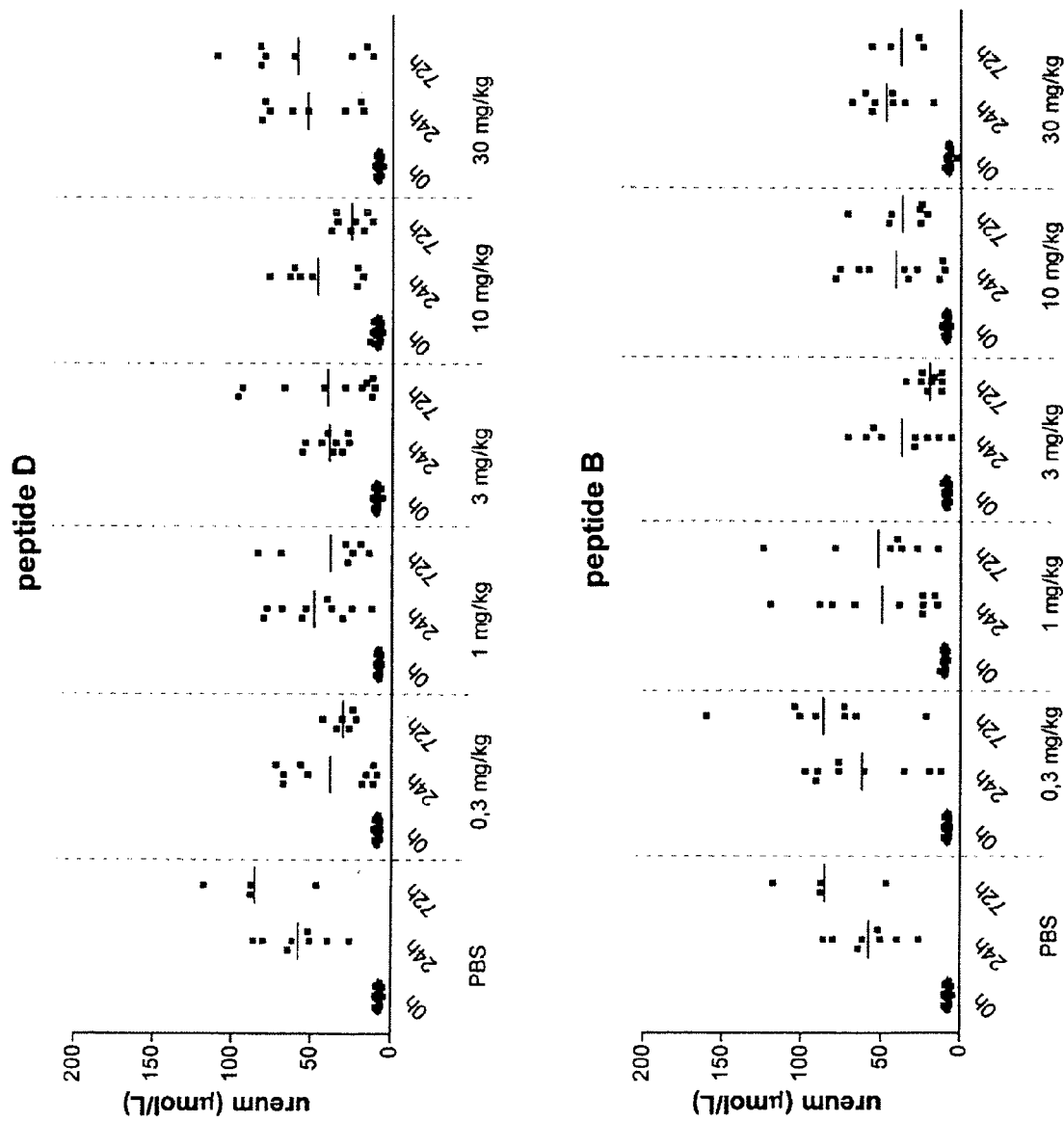
FIG. 3 depicts the blood urea values of Example 4 at 0, 24, and 72 hours post-clamping after administration of "peptide D" AQG and "peptide B" AQGV (SEQ ID NO:2). PBS control compared to peptide administered groups.

TABLE 5 statistical significance/p values (Mann Whitney U-Test) of serum urea levels in dose-response experiment 72 hours post-clamping. PBS control compared to peptide administered groups. (See, FIG. 3).

|  | 72 h |
| --- | --- |
| PBS | NA |
| AQG 0.3 mg/kg | 0.001 |
| AQG 1.0 mg/kg | 0.009 |
| AQG 3.0 mg/kg | 0.02 |
| AQG 10.0 mg/kg | 0.000 |
| AQG 30.0 mg/kg | 0.23 |
| AQGV (SEQ ID NO: 2) 0.3 mg/kg | 0.88 |
| AQGV (SEQ ID NO: 2) 1.0 mg/kg | 0.054 |
| AQGV (SEQ ID NO: 2) 3.0 mg/kg | 0.000 |
| AQGV (SEQ ID NO: 2) 10.0 mg/kg | 0.001 |
| AQGV (SEQ ID NO: 2) 30.0 mg/kg | 0.003 |

What is claimed is:

1. An isolated oligopeptide consisting of the amino acid sequence of SEQ ID NO: 2 or a pharmaceutically acceptable salt thereof.

2. A pharmaceutical composition comprising a peptide consisting of the amino acid sequence of SEQ ID NO: 2 or a pharmaceutically acceptable salt thereof.

3. The pharmaceutical composition of claim 2 further comprising a pharmaceutically acceptable carrier, adjuvant, diluent, excipient or any mixtures thereof.

4. An isolated oligopeptide consisting of the amino acid sequence of SEQ ID NO: 2.

* * * * *

UNITED STATES PATENT AND TRADEMARK OFFICE
CERTIFICATE OF CORRECTION

PATENT NO. : 7,576,174 B2
APPLICATION NO. : 11/346450
DATED : August 18, 2009
INVENTOR(S) : Benner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 483 days.

Signed and Sealed this

Seventh Day of September, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 1

Met Thr Arg Val
1

<210> SEQ ID NO 2
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 2

Ala Gln Gly Val
1

<210> SEQ ID NO 3
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 3

Leu Gln Gly Val
1

<210> SEQ ID NO 4
<211> LENGTH: 4
<212> TYPE: PRT
<213> ORGANISM: Artificial Sequence
<220> FEATURE:
<223> OTHER INFORMATION: Synthesized Peptide

<400> SEQUENCE: 4

Leu Ala Gly Val
1

<210> SEQ ID NO 5
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 5

Val Leu Pro Ala Leu Pro Gln
1               5

<210> SEQ ID NO 6
<211> LENGTH: 6
<212> TYPE: PRT
<213> ORGANISM: Artificial Sequence
<220> FEATURE:
<223> OTHER INFORMATION: Synthesized Peptide

```
-continued

<400> SEQUENCE: 6

Val Leu Pro Ala Leu Pro
1               5
```